US010398321B2

(12) United States Patent
Zhang (10) Patent No.: US 10,398,321 B2
(45) Date of Patent: *Sep. 3, 2019

(54) THERMAL PATIENT SIGNAL ANALYSIS

(71) Applicant: Siemens Medical Solutions USA, Inc., Malvern, PA (US)

(72) Inventor: Hongxuan Zhang, Palatine, IL (US)

(73) Assignee: Siemens Healthcare GmbH, Erlangen (DE)

(*) Notice: Subject to any disclaimer, the term of this patent is extended or adjusted under 35 U.S.C. 154(b) by 117 days.

This patent is subject to a terminal disclaimer.

(21) Appl. No.: 14/842,606

(22) Filed: Sep. 1, 2015

(65) Prior Publication Data

US 2017/0055849 A1    Mar. 2, 2017

(51) Int. Cl.
| | | |
|---|---|---|
| *A61B 5/0205* | (2006.01) | |
| *G06F 19/00* | (2018.01) | |
| *A61B 5/01* | (2006.01) | |
| *A61B 5/1455* | (2006.01) | |
| *A61B 5/00* | (2006.01) | |
| *G16H 15/00* | (2018.01) | |

(52) U.S. Cl.
CPC .......... *A61B 5/02055* (2013.01); *A61B 5/01* (2013.01); *A61B 5/14552* (2013.01); *A61B 5/7235* (2013.01); *A61B 5/7267* (2013.01); *A61B 5/7282* (2013.01); *G06F 19/3418* (2013.01); *G16H 15/00* (2018.01)

(58) Field of Classification Search
CPC ... A61B 5/02055; A61B 5/01; A61B 5/14552; A61B 5/7235; G06F 19/3418; G06F 19/3487

USPC ................ 128/920–925; 374/100–107; 600/300–301, 473–475, 481, 483, 500, 600/508, 513–519, 526, 549

See application file for complete search history.

(56) References Cited

U.S. PATENT DOCUMENTS

| | | | |
|---|---|---|---|
| 4,834,107 | A | 5/1989 | Warner et al. |
| 5,025,795 | A | 6/1991 | Kunig et al. |
| 5,251,626 | A | 10/1993 | Nickolls et al. |
| 5,486,204 | A | 1/1996 | Clifton et al. |
| 5,535,753 | A * | 7/1996 | Petrucelli ............... A61B 5/021 600/485 |
| 5,797,395 | A | 8/1998 | Martin et al. |
| 6,004,274 | A | 12/1999 | Nolan et al. |
| 6,186,955 | B1 | 2/2001 | Baura et al. |
| 6,322,514 | B1 | 11/2001 | Holte et al. |
| 6,582,656 | B1 | 6/2003 | Steuer et al. |
| 6,757,554 | B2 | 6/2004 | Rubinstein et al. |
| 6,829,501 | B2 | 12/2004 | Nielsen et al. |
| 7,024,244 | B2 | 4/2006 | Muhlenberg et al. |
| 7,220,230 | B2 | 5/2007 | Roteliuk et al. |
| 7,422,562 | B2 | 9/2008 | Hatib et al. |

(Continued)

*Primary Examiner* — Gary Jackson
*Assistant Examiner* — Jonathan Kuo (57) ABSTRACT

Disclosed herein is a framework for facilitating thermal patient signal analysis. In accordance with one aspect, the framework receives patient signal data including thermal signal data. The framework then segments a waveform of the thermal signal data into portions and extracts thermal parameters based on the segmented portions. The framework then determines one or more thermal indices based at least in part on the thermal parameters and generates a report that presents cardiac event detection results determined based at least in part on the one or more thermal indices.

18 Claims, 8 Drawing Sheets

(56) References Cited

U.S. PATENT DOCUMENTS

| | | |
|---|---|---|
| 7,485,094 B2 | 2/2009 | Marks et al. |
| 7,744,594 B2 | 6/2010 | Yamazaki et al. |
| 7,871,408 B2 | 1/2011 | Krishnan et al. |
| 7,925,347 B1 | 4/2011 | Bornzin et al. |
| 8,116,849 B2 | 2/2012 | Zhang et al. |
| 8,187,198 B2 | 5/2012 | Bhunia et al. |
| 8,255,052 B2 | 8/2012 | Salo et al. |
| 8,801,618 B2 | 8/2014 | Hatib et al. |
| 2008/0045847 A1* | 2/2008 | Farag ............... A61B 5/02055 600/500 |
| 2010/0185084 A1* | 7/2010 | Zhang ............... A61B 5/029 600/425 |
| 2010/0280396 A1* | 11/2010 | Zhang ............... A61B 5/021 600/485 |
| 2011/0224564 A1* | 9/2011 | Moon ............... A61B 5/00 600/509 |
| 2012/0179382 A1* | 7/2012 | Zhang ............... A61B 5/02416 702/19 |
| 2013/0310660 A1* | 11/2013 | Zuckerman-Stark .... A61B 5/02 600/301 |
| 2014/0276090 A1* | 9/2014 | Breed ............... A61B 5/18 600/473 |
| 2016/0287096 A1* | 10/2016 | Zhang ............... A61B 5/02055 |

* cited by examiner

THERMAL PATIENT SIGNAL ANALYSIS

TECHNICAL FIELD

The present disclosure generally relates to systems and methods for analyzing thermal patient signals.

BACKGROUND

The most frequent killer of Americans is coronary artery disease (CAD) and heart-related problems, accounting for nearly 600,000 deaths each year. Studies estimate that 50% of men and 33% of women under the age of 45 will develop some form of CAD sometime during their lifetime. Sudden cardiac death has steadily accounted for approximately 50% of all heart-related, out-of-hospital deaths and improved clinical procedures almost entirely ignore this group. The fact that patients generally fail to recognize their symptoms and to seek prompt medical attention contributes to these tragic statistics.

The cardiovascular system has three components: (1) a pump (or heart); (2) a carrier fluid (or blood); and (3) a distribution system (or arteries), an exchange system (or capillary network) and a collecting system (or venous system). Blood pressure is the driving force that propels blood along the distribution network. The blood vessels include arteries, arterioles, capillaries, venules and veins. Blood is carried in these vessels. The arteries, which are strong, flexible, and resilient, carry blood away from the heart and bear the highest blood pressures. Because arteries are elastic, they recoil passively when the heart is relaxing between beats, thus helping to maintain blood pressure. Arteries branch into smaller and smaller vessels, eventually becoming very small vessels called arterioles. Arteries and arterioles have muscular walls that can adjust their diameters to increase or decrease blood flow to a particular part of the body.

The principal manifestations of CAD are coronary atherosclerosis (hardening of the coronary arteries) or stenosis (narrowing of the arteries), both of which ultimately force a reduction in coronary circulation and result in low blood flow and less blood volume from heart to body. During cardiac arrhythmia, various portions of heart muscle receive less oxygen that can ultimately lead to irreversible scarring and necrosis of the muscle tissue (myocardial infarction), reducing the efficiency with which the heart can pump blood to the rest of the body and possibly leading to fatal cardiac arrhythmias.

Hemodynamic signals (e.g., pressure, pulse, temperature and thermal signals) related to blood flow from heart to human body surface vessels may be analyzed to characterize cardiac pathology and disorders, and even predict life-threatening events. However, traditional methods focus on stroke volume and cardiac output calculation, which do not fully capture waveform information from the patient blood pressure signals. Other known clinical methods for cardiac arrhythmia detection require extensive clinical experience and knowledge of these approaches, such as interpretation of the parameters, calculation accuracy, etc., which may pose limitations for some medical users.

Known cardiac arrhythmia characterization approaches are mostly based on electrocardiography (ECG) and other electrophysiological activity signals. However, cardiac chamber malfunctions and clinical events affect the tissue and hemodynamic signals much earlier than electrophysiological signals.

Current hemodynamic parameter-based cardiac arrhythmia detection methods (e.g., invasive blood pressure or IBP) are typically invasive. Known thermodilution methods in heart calculation typically involve acquiring an invasive injection waveform. Current non-invasive methods include image-based cardiac pathology detection methods, such as fluroscopic image scanning and ultrasound image scanning, which require measurement of a two-dimensional (2D) or three-dimensional (3D) heart image to calculate its size and volume. Such methods are typically inaccurate, especially for end-of-diastole (EoD) and end-of-systole (EoS) timing-based size measurement.

Additionally, most known clinical methods for cardiac arrhythmia diagnosis focus on linear relations between signal waveform morphology and cardiac diseases. However, relations between cardiac arrhythmia and patient signals are actually nonlinear. Therefore, current clinical methods can only achieve non-accurate functionality diagnosis.

In addition, in most clinical environments (e.g., operating room, catheter lab, etc.), there is a lot of unwanted but unavoidable electrical noise, such as power emission noise, electrical stimulating noise, electrical cutter noise, etc. Such noise can easily affect electrophysiological signals (e.g., ECG signals).

Currently, traditional methods for cardiac arrhythmia analysis provide qualitative evaluation of cardiac events. There are no efficient methods for quantitative characterization of cardiac pathology severity. Furthermore, known cardiac arrhythmia event detection algorithms may cause false alarms arising from analysis of a single parameter, such as magnitude of ST segment from surface ECG data. Known medical applications also require better methods to more accurately and timely characterize and predict cardiac arrhythmia events.

SUMMARY

The present disclosure relates to a framework for facilitating non-invasive thermal signal analysis. In accordance with one aspect, the framework receives patient signal data including thermal signal data. The framework then segments a waveform of the thermal signal data into portions and extracts thermal parameters based on the segmented portions. The framework then determines one or more thermal indices based at least in part on the thermal parameters and generates a report that presents cardiac event detection results determined based at least in part on the one or more thermal indices.

This summary is provided to introduce a selection of implementations in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Further

DETAILED DESCRIPTION

In the following description, numerous specific details are set forth such as examples of specific components, devices, methods, etc., in order to provide a thorough understanding of embodiments of the present disclosure. It will be apparent, however, to one skilled in the art that these specific details need not be employed to practice embodiments of the present disclosure. In other instances, well-known materials or methods have not been described in detail in order to avoid unnecessarily obscuring embodiments of the present disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

It is to be understood that the system and methods described herein may be implemented in various forms of hardware, software, firmware, special purpose processors, or a combination thereof. Preferably, the present disclosure is implemented in software as an application (e.g., n-tier application) comprising program instructions that are tangibly embodied on one or more program storage devices (e.g., magnetic floppy disk, RAM, CD ROM, ROM, etc.), and executable by any device or machine comprising suitable architecture. If written in a programming language conforming to a recognized standard, sequences of instructions designed to implement the methods can be compiled for execution on a variety of hardware platforms and for interface to a variety of operating systems. In addition, embodiments of the present framework are not described with reference to any particular programming language. It will be appreciated that a variety of programming languages may be used to implement embodiments of the present disclosure.

Cardiac events, such as Atrial Fibrillation (AF), Acute Myocardial Ischemia (AMI) and Myocardial Infarction (MI), are the most common pathologies that contribute to significant risks of electrophysiological disorders, leading to morbidity and mortality. ECG and intra-cardiac electrogram (ICEG) signals are usually utilized to diagnose ventricular arrhythmia, especially ventricular tachycardia (VT), ventricular fibrillation (VF), ventricular infarction, etc. However, long term monitoring of ECG and ICEG signals usually requires a lot of resources, experience and time, and may be complicated and risky due to, for example, invasive signal acquisition.

One aspect of the present framework facilitates cardiac arrhythmia or pathology detection based on cardiac pulse thermal (heat or temperature) signal data. Thermal signal data may be non-invasively acquired using, for example, a multi-channel body sensor system. The thermal signal data may include body surface artery blood flow thermal signal data, such as wrist thermal pulse waveforms. Such thermal signal data may be segmented into one or more portions and used to characterize cardiac pathology-related waveform changes, such as amplitude, time duration, energy, frequency, time-frequency distribution, etc. Such waveform changes may be used to qualitatively and quantitatively diagnose heart activity and cardiac arrhythmia status. By calculating the non-invasive thermal signal mode index, time, characteristics (e.g., location, severity, trend, etc.) of cardiac pathology or clinical events may be more sensitively, precisely and reliably determined, differentiated and/or predicted.

Figure 1:
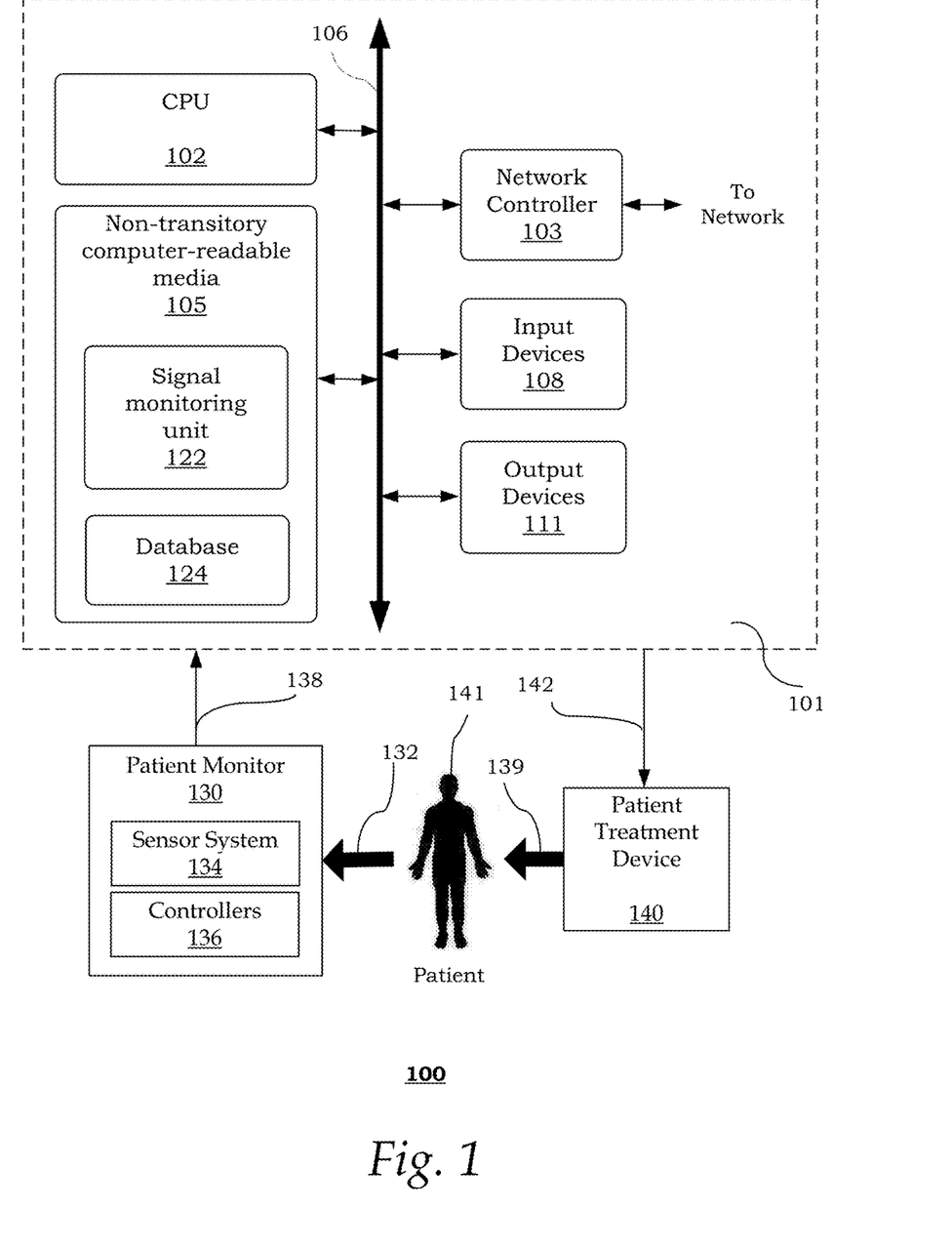
- FIG. 1 shows an exemplary system.

FIG. 1 shows an exemplary system 100 for implementing a method and system of the present disclosure. It is to be understood that, because some of the constituent system components and method steps depicted in the accompanying figures can be implemented in software, the actual connections between the system components (or the method steps) may differ depending upon the manner in which the present framework is programmed. For example, the system 100 may be implemented in a client-server, peer-to-peer (P2P) or master/slave configuration. In such configurations, the system 100 may be communicatively coupled to other systems or components via a network, such as an Intranet, a local area network (LAN), a wide area network (WAN), a P2P network, a global computer network (e.g., Internet), a wireless communication network, or any combination thereof. Given the teachings of the present disclosure provided herein, one of ordinary skill in the related art will be able to contemplate these and similar implementations or configurations of the present disclosure.

As shown in FIG. 1, the system 100 may include a computer system 101, a patient monitor 130 and a patient treatment device 140. The computer system 101 may include, inter alia, a central processing unit (CPU) or processor device 102, a non-transitory computer-readable media 105, one or more output devices 111 (e.g., printer, display monitor, projector, speaker, etc.), a network controller 103, an internal bus 106 and one or more input devices 108 such as, for example, a keyboard, mouse, touch screen, gesture and/or voice recognition module, etc. Computer system 101 may further include support circuits such as a cache, a power supply, clock circuits and a communication bus. Various other peripheral devices, such as additional data storage devices and printing devices, may also be connected to the computer system 101.

The present technology may be implemented in various forms of hardware, software, firmware, special purpose processors, or a combination thereof, either as part of a microinstruction code or as part of an application program or software product, or a combination thereof, which is executed via the operating system. In one implementation, the techniques described herein are as computer-readable program code tangibly embodied in non-transitory computer-readable media 105. Non-transitory computer-readable media or memory device 105 may include random access memory (RAM), read only memory (ROM), magnetic floppy disk, flash memory, and other types of memories, or a combination thereof. The present techniques may be implemented by signal monitoring unit 122 that is stored in computer-readable media 105. As such, the computer system 101 is a general-purpose computer system that becomes a specific-purpose computer system when executing the computer-readable program code.

The same or different computer-readable media 105 may be used for storing a database 124. Database 124 may include a repository of determined parameters, indices and/or ratios, selectable predetermined functions, patient signal data (e.g., temperature, heat, thermal, non-invasive blood pressure (NIBP) signal data, oximetric (SPO2) signal data, electrophysiological signal data such as electrocardiograms (ECG), intra-cardiac electrograms (ICEG), respiration signal data, hemodynamic or vital sign data, etc.), patient data (e.g., demographic data, pathology history, etc.), other input data and/or other derived output parameters.

In some implementations, system 100 provides a closed loop framework for real-time and adaptive monitoring and treatment of a patient 141. One or more components of system 100 (e.g., computer system 101 and patient monitor 130) may be implemented in a critical care, medical recording or monitoring device, which may be a stationary (e.g., bedside), mobile or portable system, or implemented on the patient's body.

In some implementations, computer system 101 filters and/or converts patient signal data 132 measured or acquired by patient monitor 130. Exemplary types of patient signal data include, but are not limited to, non-invasive thermal (or heat) signals from any available spots of the body surface of patient 141. Other types of patient signals, such as ECG signal, NIBP signal, SPO2 signal, other vital sign signal, and so forth, may also be measured or acquired. Further, system 101 may determine and display indices or parameters determined based on the patient signal data. System 101 may further be used to capture all disease-related patient signal distortions and predict life-threatening events. It should be appreciated that one or more functions of computer system 101 may also be performed by patient monitor 130.

As shown in FIG. 1, system 101 may be communicatively coupled to patient monitor 130 via communication channel 138 (e.g., wireless or wired) to receive patient signal data. Patient monitor 130 may include a multi-sensor or probe module 134 and controllers 136. Patient monitor 130 may further include an indicator, internal power supply (e.g., battery) or an interface device to receive power from an external power supply (e.g., wired interface or wireless power-voltage converter), as well as other components (e.g., display, memory, etc.). In some implementations, patient monitor 130 is implemented in a smart device (e.g., smart watch or other wearable device, etc.) that can be used for monitoring thermal signals. For example, a smart watch may be positioned on the patient's body to perform Holter analysis to monitor healthy status or characterize arrhythmia severity.

Sensor system 134 may include one or more different kinds of thermal sensors with different size, resolution, etc. for acquiring thermal signal data from the surface of the patient's body. Thermal sensors may also be referred to herein as temperature or heat sensors. Thermal sensors may be contact or non-contact sensors. Different sensors and/or probes may be utilized for different positions and clinical applications. Sensor system 134 may include, for example, an infrared heat-sensitive sensor, temperature-sensitive impedance sensor, chemical action temperature-sensitive heat sensor, semiconductor temperature-sensitive sensor, etc. In some implementations, high resolution and sensitivity sensors or probes are used to capture thermal modes (or patterns) for the main working temperature range (e.g., 30 to 50 degrees Celsius) of human body temperature. Other data ranges may also be used. Sensor system 134 may further include non-thermal sensors, such as an electrocardiogram sensor, a non-invasive blood pressure sensor or an oximetric (e.g., SPO2) sensor, to acquire other types vital signs and/or hemodynamic signals.

System 101 may further be communicatively coupled to patient treatment device 140 via communication channel 142 (e.g., wireless or wired) to provide closed loop treatment in response to determined parameters, ratios and/or indices. Patient treatment device 140 may include, but is not limited to, an ablator, stimulator, implantable cardiac defibrillator (ICD) system, intravenous (IV) device, and so forth. System 101 may serve to convert the determined parameters, ratios and/or indices into control parameters to adjust the treatment output 139 (e.g., stimulation rate and mode, ablation (or stim) energy level and priority, ablation sequence, energy duration pacing site, ICD parameter control, hyperthermia control, etc.) of the patient treatment device 140. In some implementations, the determined parameters, ratios and/or indices are utilized to control other medical treatment, such as IV medicine delivery parameter (e.g., fluid speed, dose, etc.) For example, when the blood flow heat amplitude is decreasing or heat variation is increasing, the stimulation rate and IV drug delivery speed may be increased accordingly to maintain heart functionality to provide enough blood oxygen and nutrition to the human body and organs.

Figure 2:
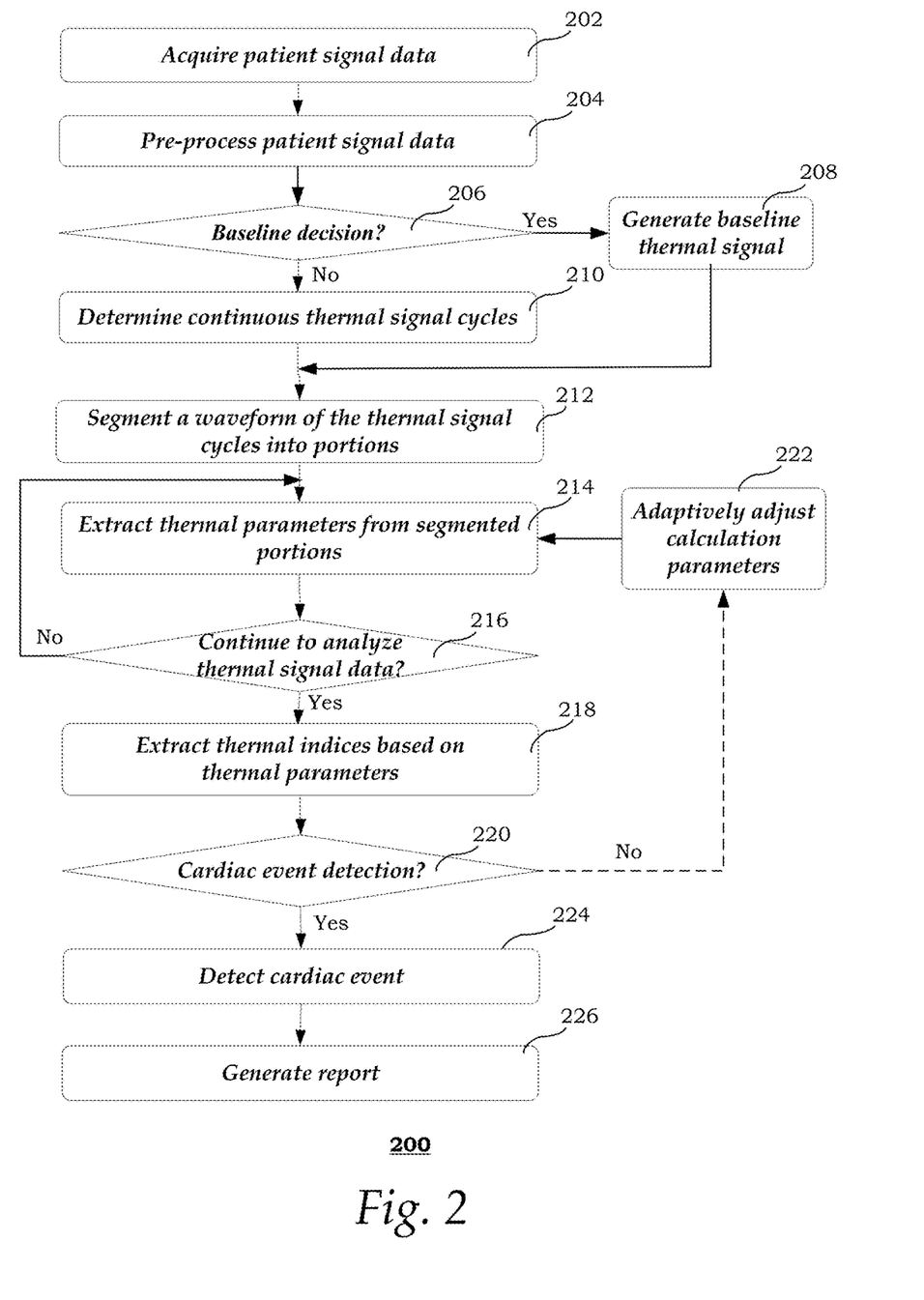
FIG. 2 shows an exemplary method of analyzing patient signal data.

FIG. 2 shows an exemplary method 200 of analyzing patient signal data. The steps of the method 200 may be performed in the order shown or a different order. Additional, different, or fewer steps may be provided. Further, the method 200 may be implemented with the system 100 of FIG. 1, a different system, or a combination thereof.

At 202, patient signal data is acquired from a patient. Such patient signal data may be represented by a waveform or graph with, for example, time represented on the horizontal x-axis and signal amplitude (e.g., temperature, voltage, etc.) represented on the vertical y-axis. Such patient signal data includes thermal signal data that is non-invasively acquired from a surface of a patient's body. Thermal signal data may include any type of signal data that is generated in response to heat from blood flowing in the blood vessels. Such thermal signal data may include, for example, temperature signals, temperature speed signals, temperature acceleration signals, thermal or heat pulse, temperature variation pulse waveforms from different locations of the body (e.g., wrist, arm, leg, forehead, etc.), and so forth. Such thermal signal data may be acquired by, for example, sensor system 134, as previously described with reference to FIG. 1.

In some implementations, the patient signal data includes cardiac electrophysiological signal data, such as electrocardiogram (ECG) data, surface ECG data, etc. Alternatively, or additionally, other types of electrophysiological signal data, such as hemodynamic (HEMO) signal data (e.g., invasive blood pressure (IBP) signal data, non-invasive blood pressure signal data, cardiac output signals, etc.), respiration (or capnographic) signal data, blood pressure data, oximetric (SPO2) signal data, capnographic signal data, temperature, and/or other vital sign signal data, other measurable patient biometric, physiological or medical signals, may also be acquired. In addition, other patient information, such as demographic data, clinical applications and patient status, including, but not limited to, weight, height, gender, age, allergies, medications, pathology history, pathology treatment history, etc., may also be acquired.

Figure 3:
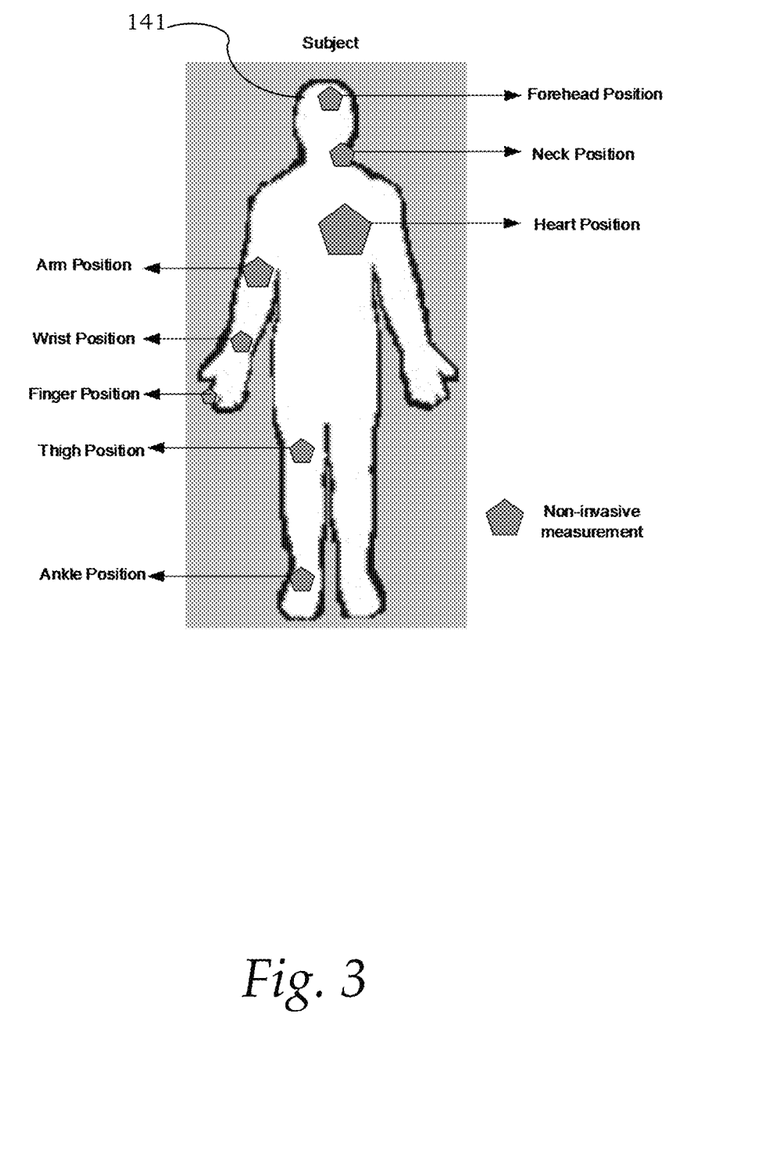
FIG. 3 shows various exemplary positions on a subject's body that may be used to non-invasively acquire patient signal data.

Thermal signal data and/or other types of patient signal data may be acquired from different parts of the body, such as around the heart position and local vessel positions. FIG. 3 shows various exemplary positions on a subject's body 141 that may be used to non-invasively acquire patient signal data. As shown, the different positions may include, but are not limited to, the forehead, neck, heart position, arm, wrist, finger (capillary system), thigh, ankle, and so forth.

According to the different positions, different kinds of thermal sensors and heat converters with different sizes, resolutions, etc. may be utilized. For example, for the wrist position, a thermistor and high resolution thermocouple may be used for recording heat and temperature mode data, such as temperature variations and instant heat changing speeds. Other types of sensors, such as infrared radiation heat sensitive sensor, temperature sensitive impedance sensor, chemical action of temperature sensitive heat sensor, semiconductor temperature sensitive sensor, etc., may also be used. Since 20 to 50 degree Celsius is the main working temperature and thermal pattern range for human body temperature, high resolution sensors or probes may be needed to best capture, detect and characterize the thermal signal pattern for cardiac pulse effects on different positions of the body surface area.

Figure 4:
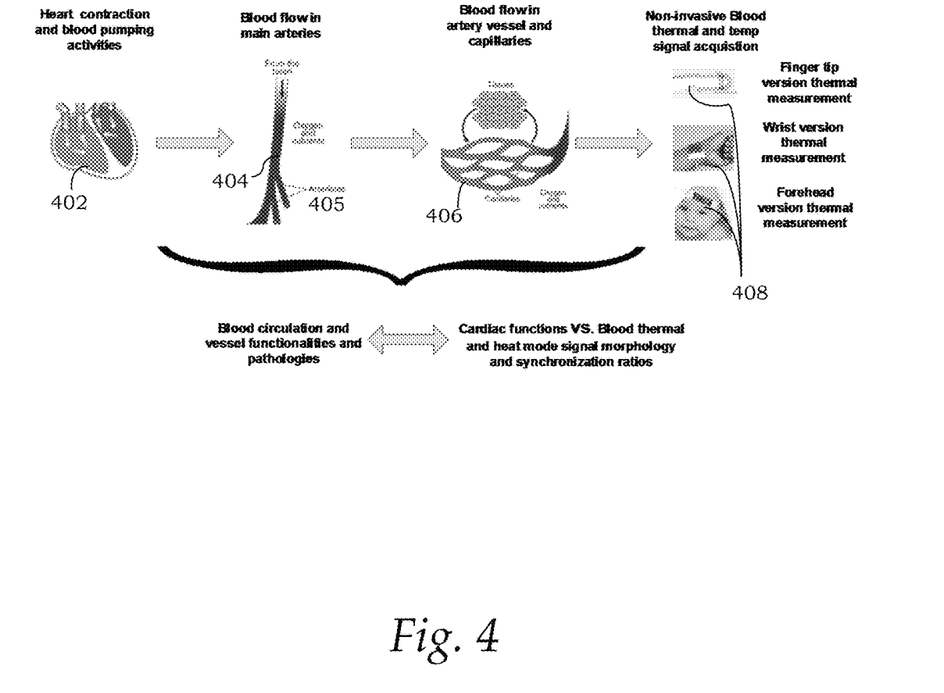
FIG. 4 illustrates a heat sensing pathway and hemodynamic link between non-invasive heat sensor signals and cardiac blood flow.

FIG. 4 illustrates a heat sensing pathway and hemodynamic link between non-invasive heat sensor signals and cardiac blood flow. Typically, blood is pumped out from left ventricular chamber 402 into the main artery 404, and then flows into sub-artery network 405, and finally into capillary vessels 406. The blood flowing in the vessels is carrying oxygen, nutrition and heat to different tissues of the human body, such as muscle, organ, etc. Blood flow thermal signals can reflect cardiac functions and blood vessel dynamic activities, such as contracting strength, energy, duration, syncing timing, etc. Thermal signal volume and amplitude reflect the blood flow, including cardiac contraction and reperfusion, which also show heart tissue functionalities and cardiac hemodynamic activities. Hence, external thermal signals can be utilized to track and characterize cardiac pathologies. For example, thermal variations on the same spot of the patient body from the blood flow mode can be utilized to qualitatively and quantitatively characterize heart chamber function changes, cardiac arrhythmia events, etc., especially the severity, type, trend, and to perform early prediction of potential cardiac emergency events.

In some implementations, blood flow circulation and blood vessel functional characteristics are monitored by using a combination of thermal signal waveform morphologies and related parameters 408. By using thermal pulse signals 408 from vessel blood flow at different positions of the body, cardiac hemodynamic functionality can be monitored and evaluated in real time, which also facilitates real time automatic treatment, such as drug delivery, ablation and stimulation control, etc.

Returning to FIG. 2, at 204, the patient signal data is pre-processed. As discussed previously, system 101 may perform the pre-processing by conditioning, filtering, converting, amplifying, digitizing, buffering, etc., patient signal data acquired by sensor system 134. For example, the patient signal data may be pre-filtered and amplified for display on, for instance, computer system 101. The patient signal data may be filtered to remove unwanted patient movement and respiratory artifacts, as well as power line noise. The filter may be adaptively selected in response to data indicating clinical application (e.g. ischemia detection application, rhythm analysis application). The patient signal data may be conditioned, converted, amplified, buffered, filtered and/or digitized to produce a continuous stream of digitized samples.

At 206, signal monitoring unit 122 determines whether a baseline decision is required. The baseline signal (or cycle) generally refers to a known reference cycle (or benign signal) with which an unknown cycle (or value) is compared when measured or assessed. The baseline signal may be used in, for example, threshold determination, computation of parameters or indices, calculation comparison (e.g., beat to beat or average), and so forth.

If the baseline is to be automatically determined, at 208, signal monitoring unit 122 automatically generates the baseline signal (or cycle). The baseline may be adaptively adjusted according to the current application and clinical requirements. Alternatively, if the baseline is not to be automatically determined, the user may manually select it via, for example, a user interface.

At 210, signal monitoring unit 122 determines continuous thermal signal cycles from the patient signal data. Continuous thermal signal cycles may be determined by, for example, detection of a key point using an amplitude threshold.

At 212, signal monitoring unit 122 segments a waveform of the thermal signal cycles into portions. The segmented portions may be within an identified region of interest (ROI), which is any portion of the thermal signal waveform that is identified for further analysis. The region of interest may include, for example, one or more continuous thermal cycles. The ROI selection may be determined based on the clinical application and associated requirements, such as timing, area, amplitude, etc. Additionally, the region of interest may be selected based on the occurrence of one or more key points (e.g., peak or maximum point) in another patient signal (e.g., ECG).

Figure 5:
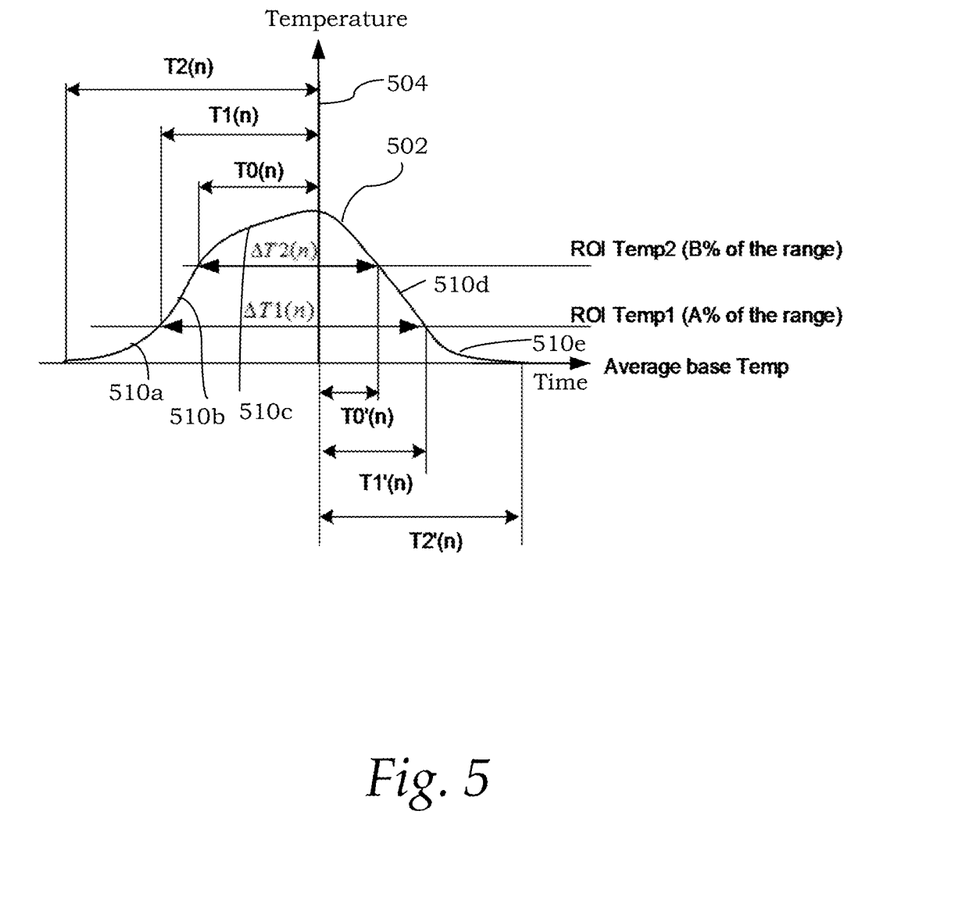
FIG. 5 shows an exemplary segmentation of a current thermal signal cycle into various portions.

In some implementations, the ROI of the thermal signal waveform is segmented based on amplitude and timing of the waveform morphology. FIG. 5 shows an exemplary segmentation of a current thermal signal cycle 502 into various portions 510a-e. The thermal signal cycle 502 is vertically separated according to temperature amplitude (T(n)). Other methods of segmentations, such as segmentation according to area (S(n)) or thermal cycle distance (TR(n)), as discussed herein, are also useful.

The amplitude threshold values for waveform segmentation, such as ROI Temp1 and ROI Temp2, may be adaptively selected as percentages (A % and B %) of the amplitude range or maximum value (T(n)). The selection of A % and B % may be performed automatically, semi-automatically or manually based on clinical application, sensitivity, ROI signal data selection, etc., to best characterize minute changes in thermal signal waveform morphology changes. Different levels and multi-level segmentations, such as C %, (A+B) %, etc., may be used to best fit the calculation according to the clinical needs. With amplitude threshold values A % and B %, different time stamps corresponding to the different waveform portions 510a-e may be determined with respect to the peak time 504 of the thermal signal waveform. The time stamps may be used to characterize the contraction and perfusion of the vessel (e.g., artery) when blood is travelling in the vessel.

Returning to FIG. 2, at 214, signal monitoring unit 122 extracts one or more thermal parameters from the segmented portions. Such thermal parameters may include, but are not limited to, time durations, time intervals, synchronization parameters, and so forth.

FIG. 5 shows various time durations and time intervals that may be extracted from a segmented n-th waveform cycle 502. As shown, time durations (e.g., T0(n), T1(n), T2(n), T0'(n), T1'(n) and T2'(n)) may be derived from the time stamps of the start and/or end point(s) of the respective segmented portions with respect to the time stamp 504 of the peak amplitude value. Additionally, time intervals of the segmented portions 510a-e may be determined. For example, time intervals ΔT1(n) is the time interval of the segmented portions 510b, 510c and 510d, while time interval ΔT2(n) is the time interval of segmented portion 510c. In some implementations, a frequency spectrum corresponding to the thermal signal cycle is also be extracted.

Figure 6:
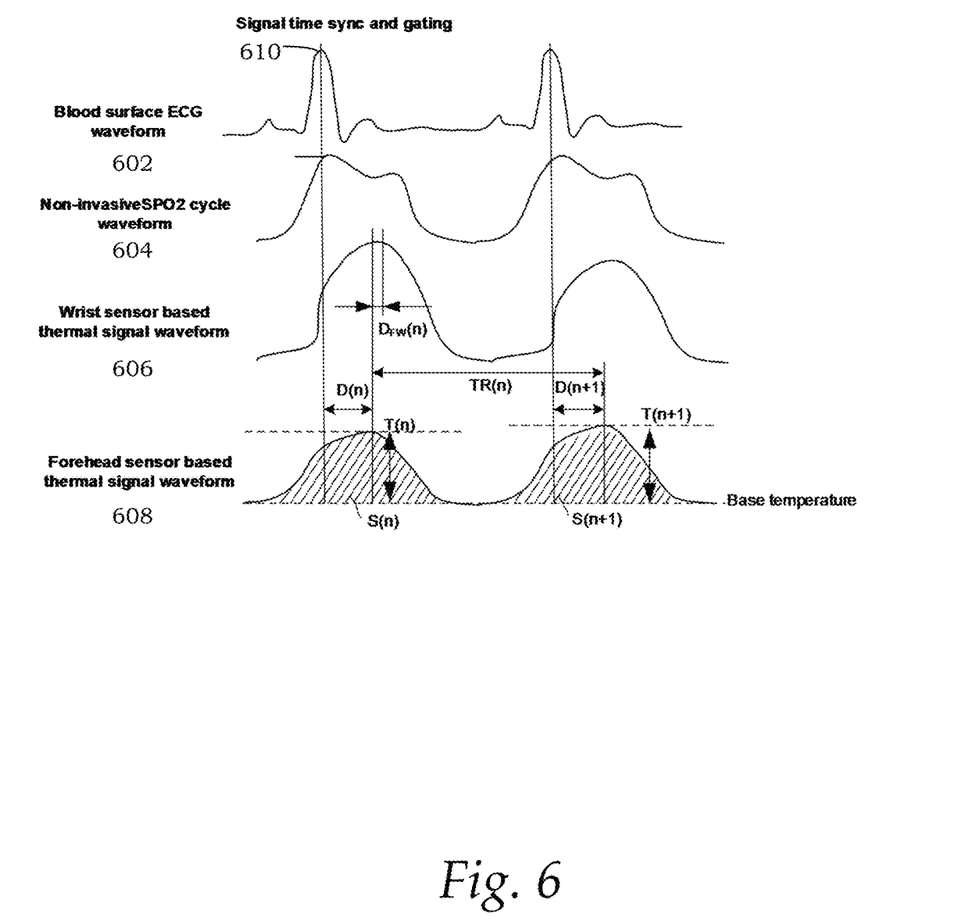
FIG. 6 shows multiple types of exemplary patient signal waveforms.

In some implementations, synchronization parameters from two different patient signals are extracted. As discussed previously, multiple kinds of non-thermal patient signals (e.g., body surface ECG, SPO2, etc.) may be simultaneously recorded and converted together with thermal signal data. FIG. 6 shows multiple types of exemplary patient signal waveforms (602, 604, 606, 608). More particularly, the patient signal waveforms may include an ECG signal waveform 602, a non-invasive oximetric (or SPO2) signal waveform 604, a first thermal (or temperature) signal waveform 606 acquired by a wrist sensor and a second thermal (or temperature) signal waveform 608 acquired by a forehead sensor. Such patient signal data may be simultaneously acquired by, for example, the sensor system 134 from different locations (e.g., fingertip, wrist, etc.) of a patient's body surface.

The first and second thermal signal waveforms (606 and 608) may be compared with either the surface ECG waveform 602 or the SPO2 signal waveform 604. A reference peak 610 of either waveform (602 or 604) may be utilized to synchronize the heart contraction (or perfusion) time stamps of the first and second thermal signal waveforms (606 and 608). It may not be necessary to monitor all other patient vital signs, electrophysiological or hemodynamic signals, to diagnose the thermal-heat signal waveform. However, if there are different kinds of the patient signals available, the analyses of multiple signals may be integrated for better sensitivity of cardiac arrhythmia detection.

In FIG. 6, two different kinds of thermal signals (606 and 608) from the wrist and forehead sensors are shown. Due to the different blood vessel sizes and blood flow speeds/volume at the wrist and forehead, the amplitudes and deviations of the first and second thermal signals (606 and 608) are slightly different. By using peak time synchronization and gating between the non-thermal signal waveform (e.g., ECG signal 602 or SPO2 signal 604) and thermal signal waveforms (606 and 608), cardiac function, such as pumping speed, heart contracting activity, etc., can be characterized to detect pathological events.

For different kinds of patient signal waveforms, different synchronization parameters may be used to capture and quantify cardiac function changes. Time durations between two ROI peaks such as time duration $D_{FW}(n)$ between the peaks of the first and second thermal signal waveforms, time duration D(n) between the peaks of the first (or second) thermal signal waveform and the ECG signal waveform, and time duration between the peaks of the first (or second) thermal signal waveform and SPO2 signal waveform, may be determined, and statistical parameters can be derived therefrom to track minute signal changes due to cardiac malfunctions. Such statistical parameters (or synchronicity values) include, for example, mean value, standard deviation, variation, etc., which can be used for quantitative and qualitative characterization of cardiac arrhythmias and will be described in more detail in the following.

Returning to FIG. 2, at 216, signal monitoring unit 122 determines if it should continue to analyze the thermal signal data. If no, the method 200 returns to 214 to extract thermal parameters. If yes, the method 200 continues to 218.

At 218, signal monitoring unit 122 extracts thermal indices based on the thermal parameters. Such thermal indices may include, but are not limited to, synchronicities, a single cycle index, a cross cycle index, and so forth. A single cycle index is determined based on parameters extracted from different portions of the same segmented cycle of a thermal signal, and may include a single time ratio (STR) and/or a single frequency ratio (SFR). A cross cycle index is determined based on parameters extracted from portions of different segmented cycles, and may include a cross time ratio (CTR), cross frequency ratio (CFR), time duration variability (TDV), and so forth. One of the segmented cycles may be a predetermined baseline cycle from a benign or pre-selected baseline signal.

In some implementations, synchronicity values between first (or second) thermal signal and a vital sign signal (e.g., ECG or SPO2) are determined as follows:

$$\text{Synchronicity\_1}(m) = \text{mean}(D(m))|_N \quad (1)$$

$$\text{Synchronicity\_2}(m) = STD(D(m))|_N \quad (2)$$

$$\text{Synchronicity\_3}(m) = \text{Var}(D(m))|_N = \frac{\text{mean}(D(m))|_N}{STD(D(m))|_N} \quad (3)$$

wherein mean(●), STD(●) and Var(●) denote average value, standard deviation index, and variation index respectively for a shifting window with a size of N cardiac cycles; and m is the cycle number for the current calculation. The time window for statistical index calculation may be automatically, semi-automatically or manually selected by software or clinical user, depending on the noise and clinical application. Usually, a 5-10 heart cycle window is selected. mean(●) denotes the mean or average value of the index in the selected window; standard deviation may be the square root of the $$\sum_{x_i \in selected\_time\_window} (x_i - \text{mean}(x_i))^2,$$

in which $x_i$ is the data series of the values within the shifting time window; Var(●) is the variation index or dispersity defined as the ratio between the mean value mean (●) and standard deviation STD(●). There may be different kinds of definitions of the unilateral syncing index and parameters, such as variability, bi-spectral, high order statistics, etc. that can be used to characterize cardiac function and event related variation.

In some implementations, synchronicity values between first and second thermal signals are determined as follows:

$$\text{Synchronicity\_4}(m) = \text{mean}(D_{FW}(m))|_N \quad (4)$$

$$\text{Synchronicity\_5}(m) = STD(D_{FW}(m))|_N \quad (5)$$

-continued $$\text{Synchronicity\_6}(m) = \text{Var}(D_{FW}(m))|_N = \frac{\text{mean}(D_{FW}(m))|_N}{STD(D_{FW}(m))|_N} \quad (6)$$

wherein mean(●), STD(●) and Var(●) denote the average value, standard deviation index and variation index respectively for a shifting window with size of N cardiac cycles; m is the cycle number for the current calculation. The time window for statistical index calculation may be automatically, semi-automatically or manually selected by software or clinical user, depending on the noise and clinical application. Usually, a 5-10 heart cycle window is selected. mean(●) denotes the mean or average value of the index in the selected window; standard deviation is the square root of the $$\sum_{x_i \in selected\_time\_window} (x_i - \text{mean}(x_i))^2,$$

in which $x_i$ is the data series of the values within the shifting time window; Var(●) is the variation index or dispersity defined as the ratio between the mean value mean(●) and standard deviation STD(●). There may be different kinds of definitions of the unilateral syncing index and parameters, such as variability, bi-spectral, high order statistics, etc., that can be used to characterize cardiac function and event related variation.

In some implementations, a single time ratio (STR) is determined as follows:

$$STR\_0(n) = \frac{T0(n)}{T0'(n)} \quad (7)$$

$$STR\_1(n) = \frac{T1(n)}{T1'(n)} \quad (8)$$

$$STR\_2(n) = \frac{T2(n)}{T2'(n)} \quad (9)$$

$$STR\_ROI_{12}(n) = \frac{\Delta T2(n)}{\Delta T1(n)} \quad (10)$$

wherein STR_0(n), STR_1(n) and STR_2(n) denote the time duration ratios of the respective time durations or time intervals derived based on the predetermined amplitude threshold levels ROI Temp1 and ROI Temp2; STR_ROI$_{12}$ is the internal time duration ratio for amplitude levels ROI Temp2 and ROI Temp1; and n denotes the current thermal signal cycle. In this calculation, each ratio represents the ratio of time lengths of heat mode rising and falling, which correspond to cardiac contraction and reperfusion activities.

In some implementations, a single frequency ratio (SFR) is determined as follows:
For example, $$SFR_{xy}(n) = \frac{f_x(n)}{f_y(n)} \quad (11)$$

$$SFR_{12}(n) = \frac{f_1(n)}{f_2(n)} \quad (12)$$

wherein SFR$_{xy}$(n) stands for the frequency (or spectral) magnitude ratio for the n-th thermal cycle; x and y denote the frequency peak numbers, and $f_x$ and $f_y$ are the frequency magnitudes of the respective peaks; SFR$_{12}$(n) is the frequency magnitude ratio between first peak and second peak of the frequency spectrum of the n-th thermal signal cycle waveform. The frequency (or spectral) magnitude or amplitude analysis actually represent the principal components of the thermal signal in the frequency domain, which enables the discovery of energy distribution changes of blood heat transmission in the blood vessel.

In some $$CTR_{01}(n) = \frac{T_0(n+1)}{T_1'(n)} \quad (13)$$

implementations, a cross time ratio (CTR) is determined as follows:

$$CTR_{ij}(n) = \frac{T_i(n+1)}{T_j'(n)} \quad (14)$$

For example,
wherein CTR$_{ij}$(n) denotes a cross time ratio of time durations or time intervals ($T_0$, $T_1$, $T_i$, $T_j$) corresponding to segmented portions of n-th and (n+1)th thermal cycles, which is segmented based on the pre-determined amplitude threshold values ROI Temp1 and ROI Temp2; n denotes the current thermal signal cycle. In this calculation, each ratio represents the ratio of time lengths of heat mode rising and falling in different thermal signal cycles, which corresponds to cardiac contraction and reperfusion activities. For example, CTR$_{11}$(n) is the cross time ratio of two signal waveforms: $T_1$(n+1) vs. $T_1$(n).

In some implementations, a cross frequency ratio (CFR) is determined as follows:

$$CFR_{xy}(n) = \frac{f_x(n+1)}{f_y(n)} \quad (15)$$

For example, $$CFR_{11}(n) = \frac{f_1(n+1)}{f_1(n)} \quad (16)$$

wherein CFR$_{xy}$(n) denotes the cross frequency (or spectral) ratio between two frequency principal components from the (n+1)-th and n-th thermal cycles; x and y denote frequency peak numbers in the thermal frequency domain, and $f_x$ and $f_y$ are the frequency magnitudes of the respective peaks; CFR$_{11}$(n) is the cross frequency ratio between first peak of the frequency spectrum of the (n+1)-th thermal cycle and first peak of the frequency spectrum of the n-th thermal cycle waveform. Such frequency magnitude ratios are actually based on principal components of the thermal signal in the frequency domain, which may enable discovery of energy distribution changes of heat transmission in the blood vessel during the transition time from n-th to (n+1)-th thermal cycles.

In some implementations, a time duration variability (TDV) is determined based on time duration or time intervals TR(n) extracted from the segmented portions as follows:

$$\text{TDV\_1}(n) = \frac{\text{mean}(TR(n))|_M}{\text{STD}(TR(n))|_M} \quad (17)$$

$$\text{TDV\_2}(n) = \frac{\text{MAX}(TR(n))|_M}{\text{STD}(TR(n))|_M} \quad (18)$$

wherein mean (●) and STD(●) denote the average value, standard deviation index and variation index respectively for a shifting window with a size of M thermal cycles; MAX(●) is the maximum cycle time length in the time shifting window M; n is the current cycle number. The time window for statistical index calculation can be selected by, for example, software or clinical user, and may depend on the noise and clinical application. For instance, a 5-10 thermal cycle window is selected, which can be adaptively adjusted.

Returning to FIG. 2, at 220, signal monitoring unit 122 determines if it should detect cardiac events. If no, the method 200 continues to 222. If yes, the method 200 continues to 224.

At 222, signal monitoring unit 122 optionally adaptively adjusts calculation control parameters used for calculating the aforementioned parameters, ratios and/or indices. The adaptive adjustment may be performed automatically, semi-automatically or manually by the clinical user based on clinical experience and knowledge. Such calculation parameters may include, but are not limited to, coefficients, calculation window sizes, signal portions, ROI, time steps, segmentation threshold levels, and so forth. Such adaptive adjustment may be performed automatically by, for example, an artificial neural network (such as the one that will be described with reference to FIG. 7), or manually based on the user's clinical experience.

At 224, signal monitoring unit 122 detects a cardiac event based on the determined thermal indices. In most cases, the aforementioned multi-sensor signal analysis can provide good sensitivity and stability for detecting cardiac events (e.g., arrhythmia). However, accuracy and reliability may be improved by combining all available patient signal data, such as other ECG signal analysis, NIBP, IBP signals analysis, etc. In some implementations, an artificial neural network (ANN) is used to nonlinearly fuse all kinds of patient data and analysis results, including the parameters and indices determined by the present framework. By using multiple types and/or channels of patient signal data, such as different lead ECG signals, NIBP, IBP, etc., cardiac arrhythmia may be more efficiently detected and characterized. For example, the ANN may facilitate identification of cardiac disorders, differentiation of arrhythmias, characterization of pathological severities, prediction of life-threatening events, and even evaluation of drug delivery and effects.

Figure 7:
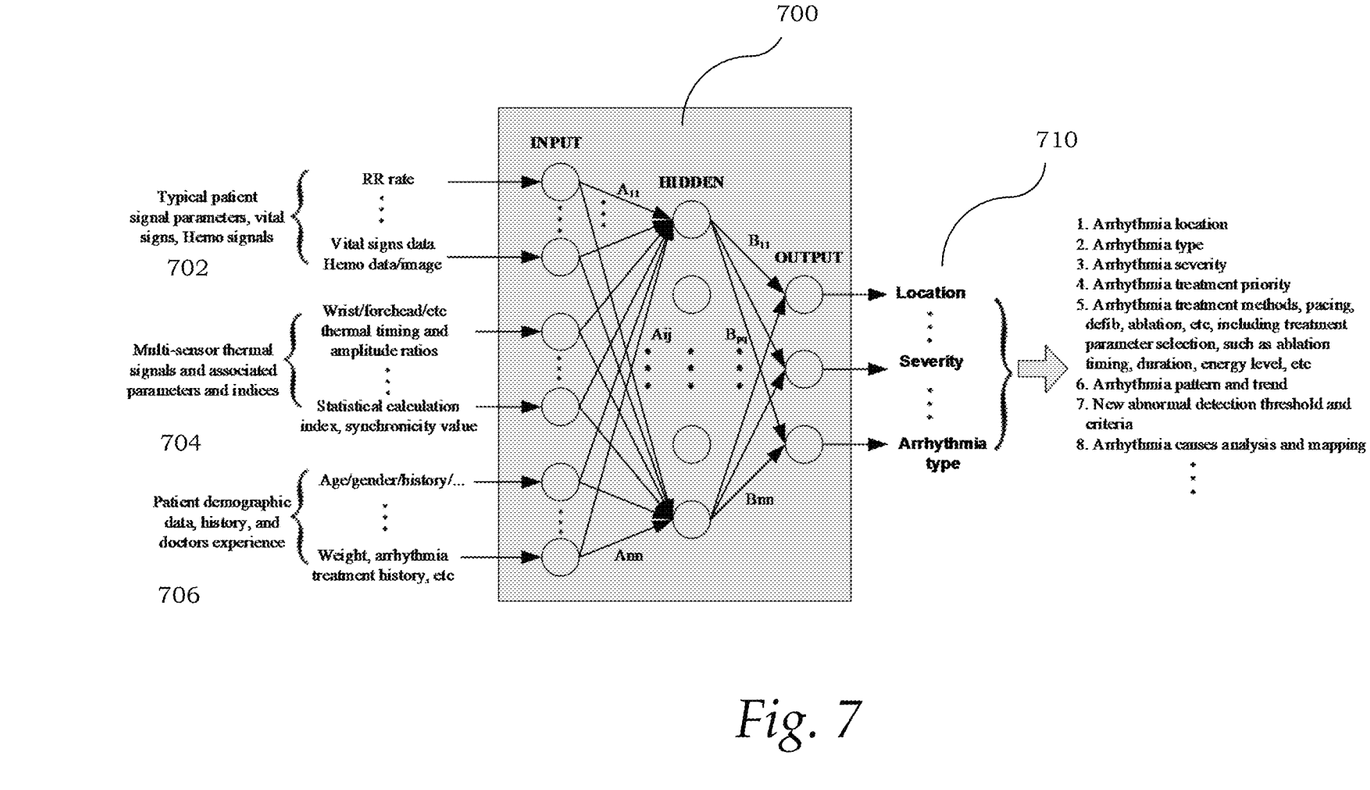
FIG. 7 shows an artificial neural network (ANN) structure.

FIG. 7 shows an artificial neural network (ANN) structure 700 for adaptive thermal signal analysis and data fusion. There ANN structure 700 has 3 layers: input layer, hidden layer and output layer. $A_{ij}$ and $B_{pq}$ are weights between the layers and they can be adaptively adjusted with a training data set. The ANN structure 700 has a self-learning ability with new input data, which advantageously increases the accuracy of the calculated results. The ANN-based analysis can be used to combine the determined thermal parameters and/or indices 704 with other types of patient data, such as other types of patient signals (e.g., RR rate, hemodynamic signals, other vital signs, etc.) and associated parameters 702, as well as patient demographic data (e.g., age, gender, clinical history, etc.) and information based on the clinician's experience 706. The ANN structure 700 may be used to generate more detailed patient status and treatment parameters 710 for optimized cardiac rhythm management (CRM). Exemplary output parameters 710 may include, but are not limited to, arrhythmia type, severity, location mapping, timing stamp, event trend, etc., as well as treatment parameter and recommendations such as treatment location, priority, treatment method (e.g., ablation, pacing, IV drug delivery, etc.), control parameters, etc.

Returning to FIG. 2, at 226, signal monitoring unit 122 generates a patient report. The patient report may present cardiac event detection results such as a cardiac abnormality, or associated characteristics (e.g., location, type, severity, timing, etc.), and other information (e.g., suggested treatment options). The patient report may be in the form of, for example, an alert message, warning or indicator. The patient report may also be stored in database 124 for future retrieval, transmitted or shared with other client computers, and/or printed in physical form for viewing. By using the present framework, cardiac functionality, especially cardiac tissue functions and activities, can be continuously monitored and quantified, which possibly facilitates early detection of clinical events and subsequent on-time treatment and drug delivery.

The present framework may be used in many clinical applications, such as operating room (OR) monitoring, intensive care unit (ICU) or critical care unit (CCU) monitoring, emergency room (ER) patient status monitoring, etc. The patient's temperature is one of the important factors for patient monitoring, and any kind of deviation may be used to timely detect a cardiac abnormality, predict patient pathology, recommend and evaluate suitable treatment.

Figure 8:
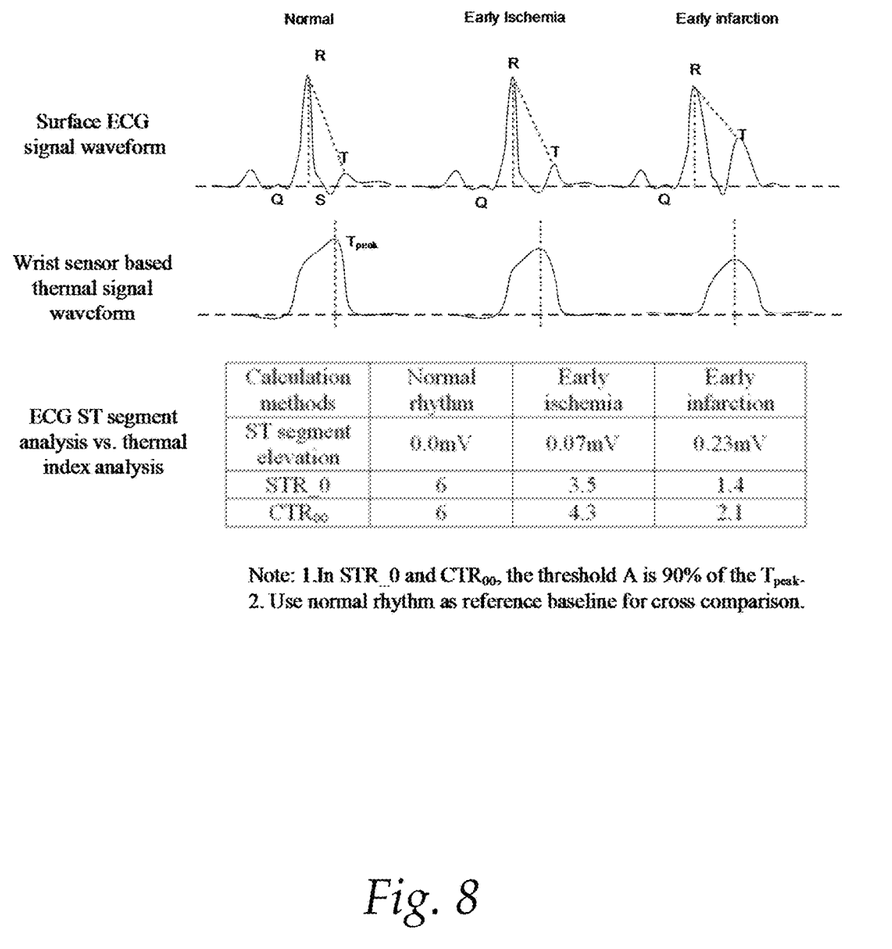
FIG. 8 shows a comparison between exemplary methods of myocardial ischemia-infarction event detection.

FIG. 8. shows a comparison between exemplary methods of myocardial ischemia-infarction event detection: ST segment elevation (clinical gold standard) and two thermal indices—STR and CTR—determined using the present framework. In the example, three different kinds of cardiac episodes (normal rhythm, early ischemia and early infarction) were simulated to generate surface ECG signal waveforms and wrist sensor-based thermal signal waveforms. The signal waveforms for these 3 episodes were characterized to compare the sensitivities of the 3 different methods. 0.1 mV detection threshold was used for the ST segment elevation method, while 20% and 50% change thresholds were utilized for the thermal indices. The results show the thermal waveform analysis may provide a valid clinical approach to detect the cardiac pathology-arrhythmia event in addition to the current clinical methods.

For simplicity, a thermal waveform area based arrhythmia severity/trend estimation is utilized for comparison. Compared to the normal rhythm, the early ischemia and infarction episode signals showed differences: 1) ST segment elevation: early ischemia signal has 0.07 mV and early infarction has 0.23 mV elevation; 2) Thermal indices $\text{STR}\_0$ and $\text{CTR}_{00}$: early ischemia values show 3.5 and 4.3 respectively, while early infarction values show 1.4 and 2.1 respectively. In the verification, 20% and 50% threshold levels were utilized to detect early ischemia and infarction respectively. The results are very good: for $\text{STR}\_0$, the deviation percentages are 42% and 77%; for $\text{CTR}_{00}$, the deviation percentages are 28% and 65%. Hence, this simulation shows that the thermal indices may provide very sensitive and accurate methods for real-time non-invasive cardiac functions tracking, severity quantification and trend prediction for cardiac arrhythmia.

While the present disclosure has been described in detail with reference to exemplary embodiments, those skilled in the art will appreciate that various modifications and substitutions can be made thereto without departing from the spirit and scope of the disclosure as set forth in the appended claims. For example, elements and/or features of different exemplary embodiments may be combined with each other and/or substituted for each other within the scope of this disclosure and appended claims.

The invention claimed is:

1. A system for patient signal analysis, comprising:
a patient monitor including a sensor system with a non-thermal sensor and multiple thermal sensors that simultaneously acquires multiple types of patient signal data including non-thermal signal data, first and second different types of thermal signal data, wherein the multiple thermal sensors acquire the first and second different types of thermal signal data that is generated in response to heat from blood flowing in blood vessels of a patient; and
a computer system communicatively coupled to the patient monitor to receive the patient signal data, wherein the computer system includes
a non-transitory memory device for storing computer readable program code, and
a processor in communication with the memory device, the processor being operative with the computer readable program code to perform steps including
determining continuous temperature cycles from the first and second different types of thermal signal data,
synchronizing a first waveform of the continuous temperature cycles from the first or second different type of thermal signal data with a second waveform of the non-thermal signal data by determining time durations between peaks of the first waveform and peaks of the second waveform within a predetermined time window,
determining at least one synchronicity value based at least in part on the time durations, and
generating a report that presents cardiac event detection results determined based at least in part on the at least one synchronicity value.

2. The system of claim 1 wherein the patient monitor comprises a smart device.

3. The system of claim 1 wherein the multiple thermal sensors acquire the first and second different types of the thermal signal data from different locations on a body surface.

4. The system of claim 1 wherein the first and second different types of the thermal signal data each comprises at least one of temperature signal data, temperature speed signal data, temperature acceleration signal data, thermal pulse or temperature variation pulse waveform.

5. The system of claim 1 wherein the processor is operative with the computer readable program code to determine one or more thermal indices based at least in part on the first and second different types of thermal signal data and the non-thermal signal data.

6. The system of claim 1 wherein the non-thermal signal data comprises electrocardiogram (ECG) signal data, oximetric signal data, or a combination thereof.

7. The system of claim 1 wherein the synchronicity value comprises a mean, standard deviation or variance of the time durations.

8. A method of patient signal analysis, comprising:
receiving, from a patient monitor, patient signal data acquired at one or more sensors and including first and second different types of thermal signal data, wherein multiple thermal sensors acquire the first and second different types of thermal signal data, wherein the first and second different types of thermal signal data is generated in response to heat form blood flowing in blood vessels of a patient;
determining continuous temperature cycles from the first and second different types of thermal signal data;
segmenting, by a computer system, a waveform of the continuous temperature cycles into portions, including separating the waveform according to temperature threshold values that are predefined as different percentages of an amplitude range of the waveform;
extracting, by the computer system, thermal parameters based on the segmented portions;
determining, by the computer system, one or more thermal indices based at least in part on the thermal parameters; and
generating, by the computer system, a report that presents cardiac event detection results determined based at least in part on the one or more thermal indices.

9. The method of claim 8 wherein extracting the thermal parameters comprises determining time durations from time stamps of start or end point of the segmented portions with respect to a time stamp of an amplitude peak of the waveform.

10. The method of claim 8 wherein extracting the thermal parameters comprises determining time intervals of the segmented portions.

11. The method of claim 8 wherein determining the one or more thermal indices comprises determining a single time ratio based on time intervals or time durations extracted from the segmented portions.

12. The method of claim 8 wherein determining the one or more thermal indices comprises determining a cross time ratio based on time intervals or time durations extracted from the segmented portions.

13. The method of claim 8 wherein determining the one or more thermal indices comprises determining a time duration variability based on time intervals or time durations extracted from the segmented portions.

14. The method of claim 8 wherein extracting the thermal parameters comprises extracting a frequency spectrum from the thermal signal data.

15. The method of claim 14 wherein determining the one or more thermal indices comprises determining a single frequency ratio based on frequency magnitudes extracted from the frequency spectrum.

16. The method of claim 14 wherein determining the one or more thermal indices comprises determining a cross frequency ratio based on frequency magnitudes extracted from the frequency spectrum.

17. The method of claim 8 further comprising:
synchronizing the waveform of the continuous temperature cycles with another waveform of the patient signal data by determining time durations between peaks of the waveform and peaks of the another waveform within a predetermined time window; and
determining a synchronicity value based at least in part on the time durations.

18. A non-transitory computer readable medium embodying a program of instructions executable by machine to perform steps for patient signal analysis, the steps comprising:
receiving patient signal data acquired at one or more sensors and including first and second different types of thermal signal data, wherein multiple thermal sensors acquire the first and second different types of thermal signal data, wherein the first and second different types of thermal signal data is generated in response to heat from blood flowing in blood vessels of a patient;

determining continuous temperature cycles from the first and second different types of thermal signal data;

segmenting a waveform of the continuous temperature cycles into portions, including separating the waveform according to temperature threshold values that are predefined as different percentages of an amplitude range of the waveform;

extracting thermal parameters based on the segmented portions;

determining one or more thermal indices based at least in part on the thermal parameters; and generating a report that presents cardiac event detection results determined based at least in part on the one or more thermal indices.

* * * * *